United States Patent [19]

Proulx et al.

[11] Patent Number: 4,679,553
[45] Date of Patent: Jul. 14, 1987

[54] VENIPUNCTURE SITE PROTECTOR

[76] Inventors: Raymond E. Proulx, 5837 Cameo, Alta Loma, Calif. 91701; Frank J. Rauscher, 5908 Mt. View Ave., San Bernardino, Calif. 92407

[21] Appl. No.: 735,331

[22] Filed: May 17, 1985

Related U.S. Application Data

[63] Continuation-in-part of Ser. No. 554,768, Nov. 23, 1983, abandoned.

[51] Int. Cl.$^4$ .............................................. A61M 5/00
[52] U.S. Cl. .............................. 128/133; 128/DIG. 6; 604/174
[58] Field of Search ......... 128/133, 154, 912, DIG. 6, 128/DIG. 26; 604/174, 175, 177, 179, 180; D24/49, 64

[56] References Cited

U.S. PATENT DOCUMENTS

| | | | |
|---|---|---|---|
| 695,270 | 3/1902 | Beringer | 128/154 |
| 3,782,377 | 1/1974 | Rychlik | 128/DIG. 6 X |
| 3,900,026 | 8/1975 | Wagner | 128/133 |
| 3,901,226 | 8/1975 | Scardenzan | 128/133 |
| 4,129,128 | 12/1978 | McFarlane | 128/133 |
| 4,517,971 | 5/1985 | Sorbonne | 128/133 |

Primary Examiner—Richard T. Stouffer
Attorney, Agent, or Firm—Boniard I. Brown

[57] ABSTRACT

A venipuncture site protector to be secured to a patient over a venipuncture site containing an intravenous needle for shielding the site and needle against contact by other objects which would cause trauma to the endothelial lining of the venal wall, pain and discomfort to the patient, and other adverse effects. The protector has a body including a relatively rigid cup-like shield of frustro-pyramidal shape and mounting tabs extending from the shield, these tabs are taped to the patient's body with the shield positioned over the venipuncture site and the intravenous needle entering the shield through a side opening. The protector body is constructed of relatively thin, stiff but readily bendable material having a low modulus of elasticity such that the protector may be bent without appreciable springback to accommodate the protector to the patient's body surface contour at the venipuncture site. The protector shield is preferably notched in a unique way which permits bending of the shield to conform to a wide range of body surface contours and body parts, including the head, arms, hands and fingers.

5 Claims, 16 Drawing Figures

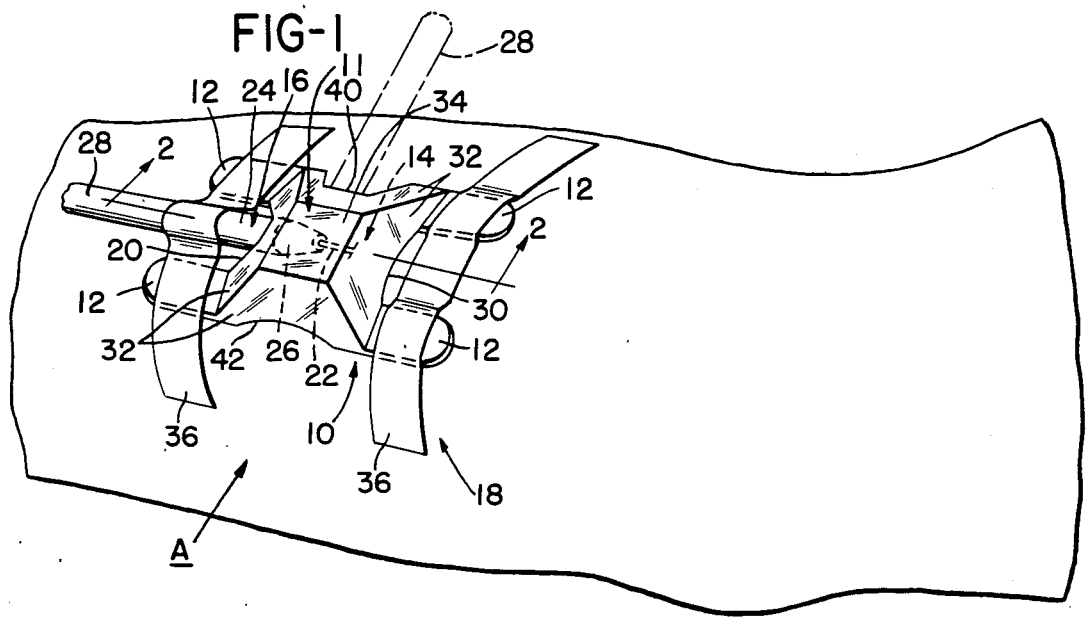
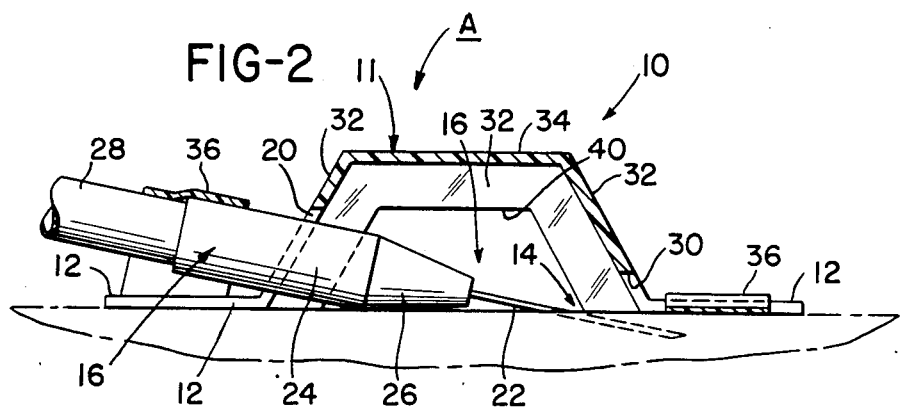
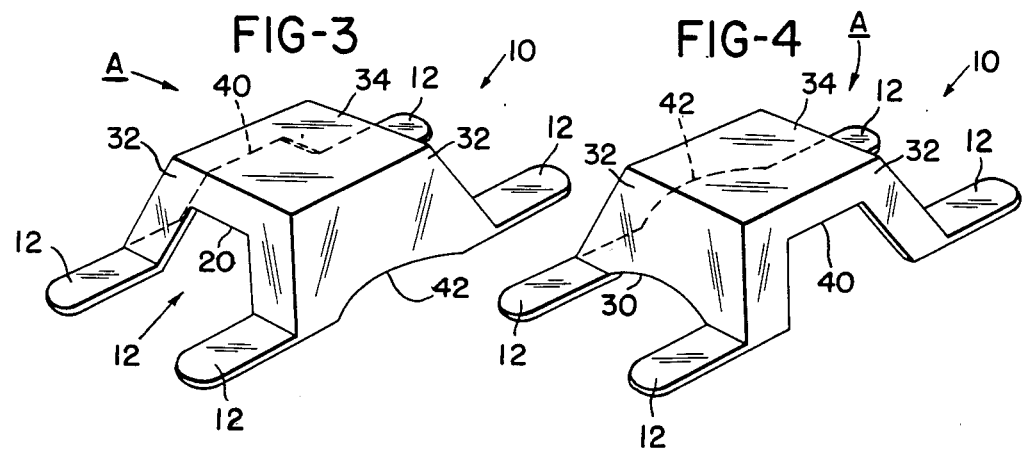

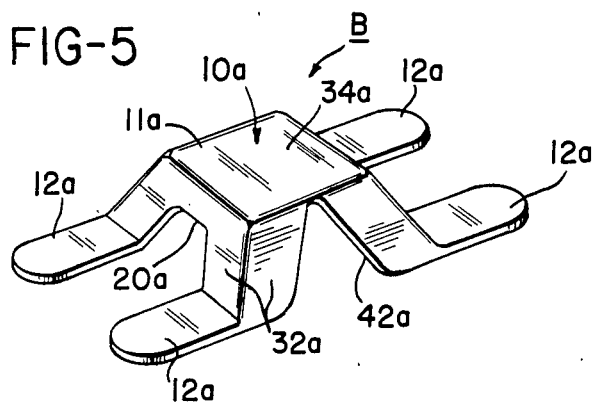
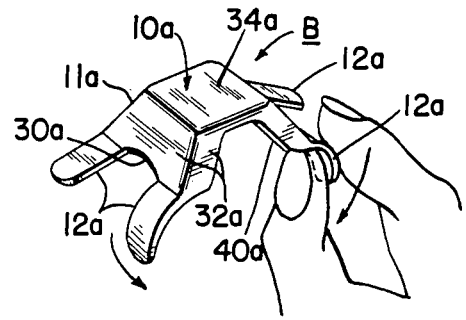
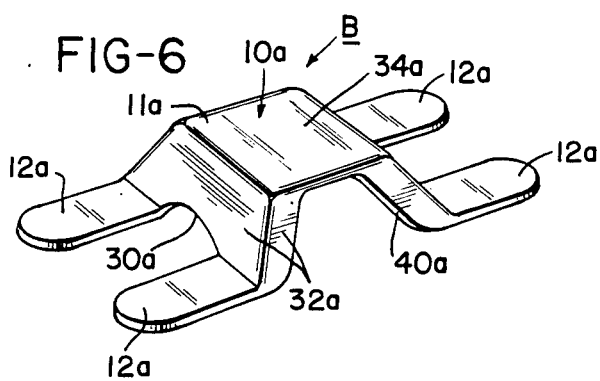
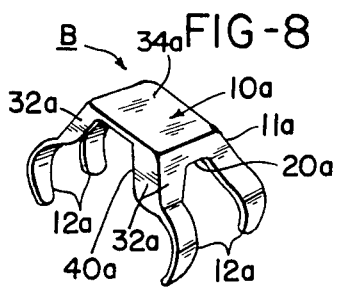
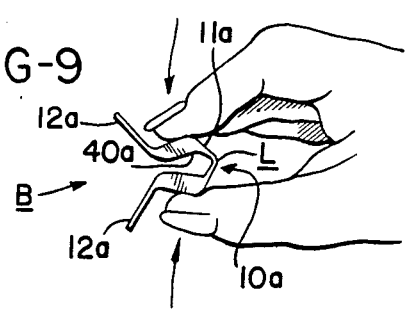
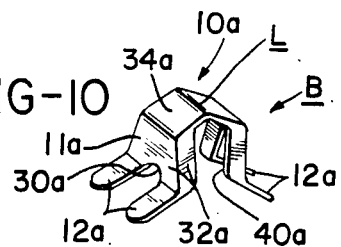
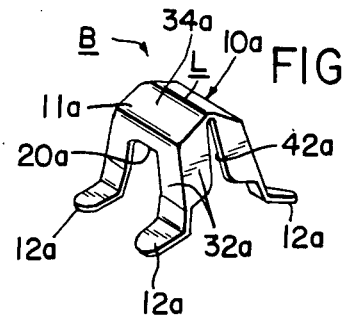
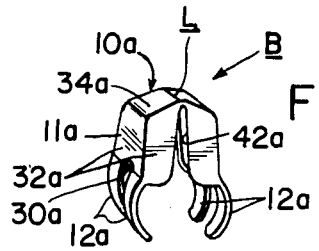

FIG-13
FIG-15
FIG-14
FIG-16
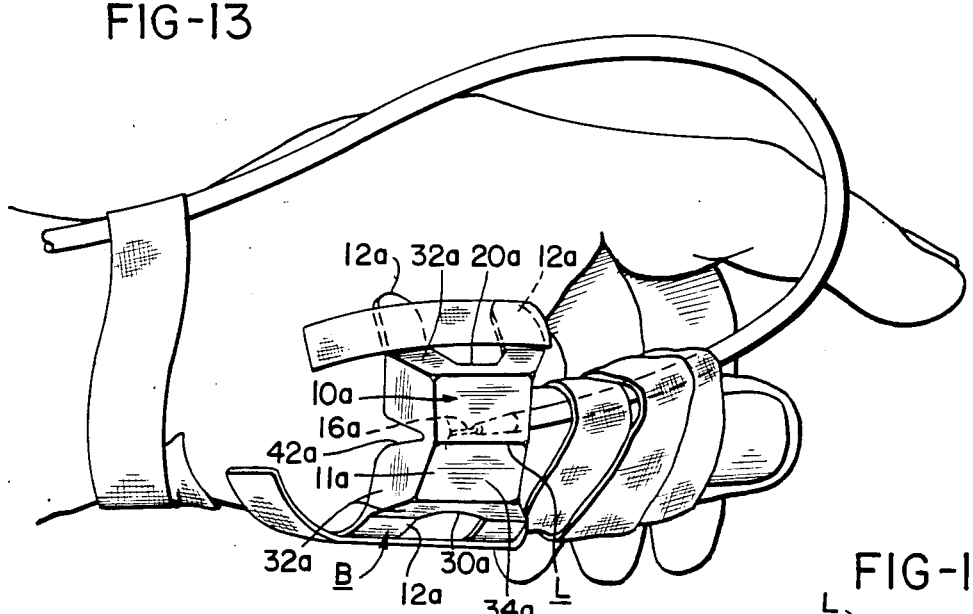
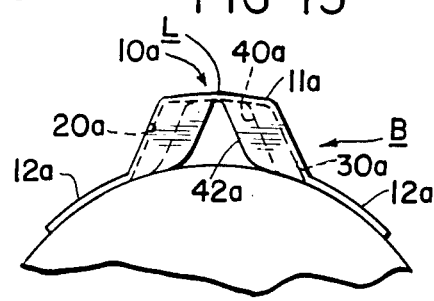
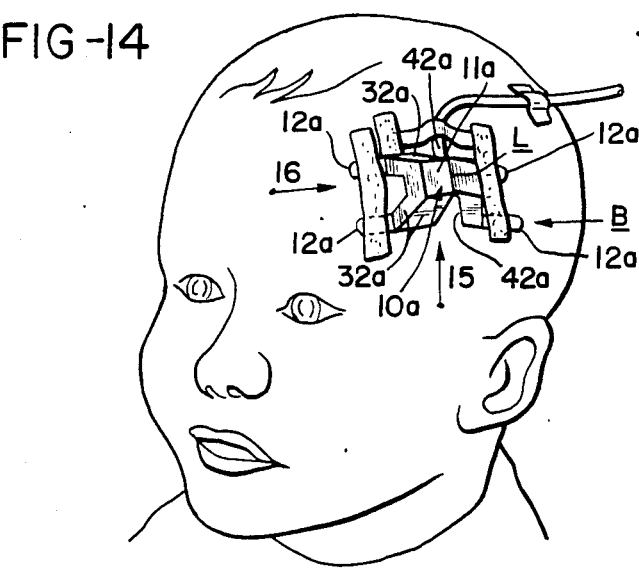
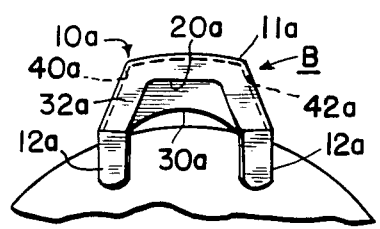

VENIPUNCTURE SITE PROTECTOR

RELATED APPLICATION

This application is a continuation-in-part of application Ser. No. 554,768, filed Nov. 23, 1983, now abandoned.

BACKGROUND OF THE INVENTION

1. Field of the Invention:

This invention relates generally to medical aids and more particularly to a novel venipuncture site protector.

2. Prior Art:

Intravenous therapy is a medical procedure involving intravenous injection of various liquids into a patient through an intravenous needle (I.V. needle) inserted into the patient's body. The place at which the needle is inserted is referred to in medical terms as the venipuncture site.

In the course of performing such intravenous therapy and otherwise caring for the patient, the venipuncture site and I.V. needle are prone to being bumped or contacted by other objects in a manner which often causes trauma to the endothelial lining of the venal wall, pain, discomfort, and other adverse effects. Elimination of this contact problem is obviously highly desirable if not essential.

A variety of intravenous therapy aids have been devised to eliminate this problem. The prior aids of which we are aware are generally devices for positioning the I.V. needle on the patient and securing the needle in a fixed relationship to the patient. Some aids include a shield for the venipuncture site, examples of such venipuncture site protectors are described in U. S. Pat. Nos. 3,900,026, 3,901,226, and 3,782,377.

SUMMARY OF THE INVENTION

This invention provides an improved venipuncture site protector for shielding the site and the I.V. needle entering the site against contact with other objects and thereby preventing trauma to the endothelial lining of the venal wall, pain, discomfort, and other adverse results of such contact.

The site protector comprises a body of relatively thin and stiff but flexible plastic or other suitable material which is preferably transparent and substantially non-resilient or non-elastic, such that the material may be readily bent without any appreciable springback. The protector body is shaped to form a relatively rigid shield of frustropyramidal shape and mounting tabs extending from the shield. The shield has an open large end, an opposite small end closed by a rectangular end wall, and four side walls which converge in the direction of and are joined to the edges of the end wall. A pair of the mounting tabs extend from each of two opposite side walls of the shield.

The venipuncture site protector is placed over a venipuncture site with the open side of the protector shield facing the site and the edge of the shield about its open side seating against the patient's skin at intervals about the site. The protector is secured to the patient by adhesive tape passing over the protector body mounting tabs.

The protector shield has a side opening or notch through which the intravenous needle enters the shield. This notch opens through the edge of the shield which seats against the patient to permit placement of the shield over the venipuncture site after insertion of the intravenous needle into the site. Preferably, the edge of the shield opposite the needle opening or notch is also notched to avoid pressing of the shield against the trauma region of the venipuncture site.

The preferred venipuncture site protectors which are illustrated and described have all four side walls of the frustropyramidal protector shield notched in such a way that the shield may receive an intravenous needle in either of two mutually orthogonal positions. According to a unique and preferred feature of the invention the notches in the two opposing shield side walls between those side walls to which the mounting tabs are joined extend substantially to the shield end wall to permit bending of the shield about a fold line of the end wall extending between the latter notches in a manner to conform the site protector to a wide range of body surface contours. This enables the protector to be applied to many different parts of the body including the head, hands, arms, and fingers.

BRIEF DESCRIPTION OF THE DRAWINGS

FIG. 1 is a perspective view of a venipuncture site protector according to the invention fixed to a patient's arm over a venipuncture site with an intravenous needle inserted into the arm at the site and illustrating in phantom lines the orthogonal needle position accommodated by the shield;

FIG. 2 is an enlarged section taken on line 2—2 in FIG. 1;

FIG. 3 is a perspective view of the venipuncture site protection shield of FIG. 1 by itself;

FIG. 4 is a perspective view of the shield similar to FIG. 3 with the shield rotated 180° to show its reverse side in FIG. 3;

FIG. 5 is a perspective view of a modified and presently preferred venipuncture site protector according to the invention;

FIG. 6 is a perspective view of the reverse side of the site protector in FIG. 5;

FIGS. 7–12 illustrate how the modified site protector may be bent to conform to a wide range of body parts and body surface contours;

FIG. 13 illustrates the modified site protector applied to a patient's hand;

FIG. 14 illustrates the modified site protector applied to a baby's head;

FIG. 15 is a view looking in the direction of arrow 15 in FIG. 14; and

FIG. 16 is a view looking in the direction of arrow 16 in FIG. 14.

DESCRIPTION OF THE PREFERRED EMBODIMENT

Referring first to FIGS. 1–4 of the drawings, the illustrated venipuncture site protector A of the invention comprises a body 10 constructed of a relatively thin, preferably relatively non-resilient or non-elastic, and relatively firm but easily bendable plastic or other material. For reasons which will be mentioned later, the site protector is preferably transparent. The protector body 10 is shaped to form a relatively rigid cup-like shield 11 of frustro-pyramidal shape and mounting tabs 12 extending from the shield. The protector is adapted to be applied to a patient with the shield 11 positioned over a venipuncture site 14 of a patient containing an inserted intravenous needle 16 to shield the site and needle against contact with other objects which would cause trauma to the endothelial lining of the venal wall, pain and discomfort to the patient, and other adverse effects.

In one side of the shield 11 is an opening or notch 20 for receiving the intravenous needle 16. As shown best in FIG. 2, this needle comprises a relatively small diameter needle tip 22 extending from a holder 24 with a tapered end 26, and a tube 28 extending from the holder to the supply of intravenous liquid to be injected into the patient. The intravenous needle 16 enters the shield through its needle opening 20 and enters the patient's skin at an oblique angle at the venipuncture site 14, as illustrated in FIG. 2.

The illustrated I.V. needle 16 is so sized that its tip 22 extends under the edge of the protector shield 11 opposite the needle opening 20. In this case, it is desirable to notch this opposing shield edge at 30 to provide a clearance between the edge and the patient's skin in order to avoid pressing of the shield against the skin over the trauma region of venipuncture site. Both the needle opening 20 and the notch 30 open through the edge of the shield 11 about its open side. Obviously, if the shield is made sufficiently large that the shield edge does not overlie the needle tip 22, the notch 30 may be eliminated, if desired.

The frustropyramidal shield 11 of the venipuncture site protector A has four tapered side walls 32 and a normally top rectangular end wall 34. The side walls 32 converge in the direction of and are joined to the edges of the top wall 34. The needle opening 20 comprises a truncated notch in one side wall 32 and the notch 30 is an arcuate recess in the opposing side wall.

The mounting tabs 12 of the protector A extend outwardly, in the plane of the large end of the shield, from the opposing shield side walls 32 which contain the needle opening 20 and recess 30. The protector is secured to the patient by adhesive strips 36 which extend over and in adhesive contact with these tabs, as shown. When the shield is in place over the venipuncture site 14, the two tabs 12 on the shield wall 32 containing the needle opening 20 straddle the intravenous needle 16. If desired, the adhesive strip 36 which extends over these latter two tabs may also extend over the needle to secure the latter in position.

In some cases, as where the venipuncture site 14 to be protected is on the patient's arm, as shown, it may be convenient to secure the site protector A to the patient in only one position (with the tabs 12, extending lengthwise of the arm, as shown for example). This means, of course, that the needle opening 20 can be oriented in only one position, or at best in only either one of the two opposite positions, such as those in which the needle opening faces lengthwise of the arm. On the other hand, it may be desirable or necessary to orient the intravenous needle 16 in a transverse position relative to that permitted by the needle opening 20.

For this reason, the venipuncture site protector A illustrated is provided with a second needle opening or notch 40 and recess 42 in the two opposing shield side walls 32 between those containing the needle opening 20 and recess 30. This second needle opening accommodates an intravenous needle transverse to the needle position permitted by the needle opening 20.

It will now be understood that the venipuncture site protector A of the invention is adapted to be secured over a venipuncture site 14 on a patient, after insertion of an intravenous needle 16 into the site, to shield the latter and needle against contact with other objects which would cause trauma, pain and/or other discomfort to the patient. The protector is preferably transparent to permit visual inspection.

The modified, presently preferred venipuncture site protector B of FIGS. 5-16 is identical to that of FIGS. 1-4 except in one very important respect which provides the modified protector with a distinct advantage over that of FIGS. 1-4. Because of their similarity, the elements of the modified protector are designated by the same reference numerals, with the subscript a as the corresponding elements of the protector A. Moreover, the description of the common structure of the modified protector will be somewhat abbreviated.

With this in mind, the modified venipuncture site protector B comprises a body 10a of the same material as the venipuncture site protector A. The material preferably has a relatively low modulus of elasticity and hence is substantially non-resilient or non-elastic so that it may be bent without any significant spring back. The protector body is shaped to form a substantially truncate or frustro-pyramidal shield 11a and mounting tabs 12a extending from two opposite sides of the shield. The shield has an open large end, an opposite small end closed by a normally top rectangular end wall 34a, and tapered side walls 32a which converge in the direction of and are joined to the edges of the top end wall.

The mounting tabs 12a are joined to two opposite shield side walls 32a in the plane of the large open end of the shield 11a. One of these side walls has an opening or notch 20a through which an I.V. needle 16a may enter the shield. The opposite shield side wall 32a has a clearance recess or notch 30a.

The modified venipuncture site protector B, as thus far described, is identical to the venipuncture site protector A of FIGS. 1-4 and is applied to the patient in the same way as the latter protector. The modified protector B differs from the protector A in the shape and depth of the notches 40a, 42a in the two opposing side walls 32a of the protector shield 11a between the two shield side walls from which extend the mounting tabs 12a. Thus, both of the notches 40a, 42a extend substantially the full length or depth of the shield 11a from its large open end to the end or top wall 34a. The notch 40a, which provides an I.V. needle entrance opening in the shield, has a truncated shape. Notch 42a which provides a clearance recess for the same purpose as recess 42 in the venipuncture site protector A, is a tapered or V-shaped notch.

As just indicated, the notches 40a, 42a serve the same purpose as the notches 40, 42 in the venipuncture site protector A. Thus, the notches 40a, 42a permit the protector B to receive an I.V. needle 16 in a direction orthogonal to the needle direction permitted by the protector shield notches 20a, 30a. The notches 40a, 42a serve one additional important function. Thus, because of the fact that the notches 40a, 42a extend the full length of the protector shield 11a from its open end to its end wall 34a, the shield 11a can bend along a fold line L lying along the intersection of the end wall and a plane containing the notches, and more specifically the center lines of the notches, as shown in FIGS. 9-12. The shield 11a is also capable of some degree of bending at right angles to the fold line L.

This bendability or flexibility of the shield 11a of the venipuncture site protector B, along with the flexibility or bendability of its mounting tabs 12a, illustrated in FIGS. 7 and 8, permit the protector to be conformed to a wide range of patient body surface contours and to be applied to virtually any part or member of the body. FIG. 13, for example, shows the protector B applied to a patient's hand. FIGS. 14–16 illustrate the protector applied to a baby's head. Obviously, the protector can be applied to other parts of the body.

The inventors claim:

1. A venipuncture site protector, comprising:

a body constructed of relatively non-elastic thin and stiff but readily bendable material and including a cup-like shield mounting tabs extending from said shield, said shield having an open end, an opposite closed end, four side walls, a rectangular end wall closing said closed end and joined along its edges to said side walls, and a generally rectangular cross section in planes parallel to said end wall, said mounting tabs including a pair of laterally spaced tabs extending outwardly from each of two opposite sides of said shield and joined to the corresponding opposite side walls of said two opposite sides along junctures disposed substantially in the plane of said open shield end, said two corresponding opposite side walls and the two remaining opposite shield side walls having end edges at said open end of said shield and notches entering said side wall edges, the notches in each pair of said opposite walls being aligned for receiving through one of said notches of each pair of said opposite side walls a holder mounting an intravenous needle entering the venipuncture site with the holder positioned within said one notch and needle extending subcutaneously toward the other notch of the respective pair of said opposite side walls, and said one notch of each pair of said opposite side walls being larger than said other notch of said opposite side wall of said pair and occupying a major portion of the respective side wall for receiving the needle holder, and said other notch of the other respective pair of said opposite side walls providing clearance for the patient's skin above the needle.

2. The venipuncture site protector of claim 1, wherein:

said one notch of each said pair of said opposite side walls is a relatively broad and deep, generally rectangular notch and the other notch of the respective wall pair is a relatively shallow arcuate recess.

3. The venipuncture site protector of claim 1, wherein:

the notches in said two remaining shield side walls extend from said side wall edges substantially to said end wall, whereby said shield is bendable about a fold line coinciding approximately with said end wall.

4. The venipuncture site protector of claim 3, wherein:

said one notch of each said pair of said opposite side walls is a relatively broad and deep, generally rectangular notch extending from the edge of the respective side wall substantially to said end wall, and the other notch of the respective side wall pair is a V notch extending from the respective side wall edge substantially to said end wall.

5. The venipuncture site protector of claim 1, wherein:

said shield has a generally frustopyramidal shape, and each pair of said opposite side walls converge toward said end wall.

* * * * *